United States Patent
Piron et al.

(10) Patent No.: US 10,241,170 B2
(45) Date of Patent: *Mar. 26, 2019

(54) SYSTEM AND METHOD FOR MAGNETIC RESONANCE IMAGE ACQUISITION

(71) Applicant: SYNAPTIVE MEDICAL (BARBADOS) INC., Bridgetown (BB)

(72) Inventors: Cameron Anthony Piron, Toronto (CA); Alexander Gyles Panther, Toronto (CA); Chad Tyler Harris, Toronto (CA); Stephen B. E. McFadyen, Toronto (CA)

(73) Assignee: SYNAPTIVE MEDICAL (BARBADOS) Inc., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/705,819

(22) Filed: Sep. 15, 2017

(65) Prior Publication Data

US 2018/0031654 A1   Feb. 1, 2018

Related U.S. Application Data

(63) Continuation of application No. 15/321,818, filed as application No. PCT/CA2014/000692 on Sep. 15, 2014, now Pat. No. 9,797,968.

(51) Int. Cl.
*G01V 3/00*   (2006.01)
*G01R 33/46*   (2006.01)
(Continued)

(52) U.S. Cl.
CPC .......... *G01R 33/4625* (2013.01); *A61B 5/055* (2013.01); *G01R 33/3621* (2013.01);
(Continued)

(58) Field of Classification Search
CPC ................................................. G01R 33/4625
(Continued)

(56) References Cited

U.S. PATENT DOCUMENTS

| 4,716,368 | A | * | 12/1987 | Haacke | G01R 33/561 |
|---|---|---|---|---|---|
| | | | | | 324/308 |
| 5,939,884 | A | | 8/1999 | Goldfarb et al. | |
| 9,797,968 | B2 | * | 10/2017 | Piron | G01R 33/4625 |

OTHER PUBLICATIONS

Oh C H et al., "Dynamic range expansion of receiver by using optimized gain adjustment for high-field MRI", Concepts in Magnetic Resonance Part A, vol. 36A, No. 4, Jul. 2010, pp. 243-254, XP55482698.

(Continued)

*Primary Examiner* — Louis Arana
(74) *Attorney, Agent, or Firm* — Perry + Currier Inc.

(57) ABSTRACT

A system and method of acquiring an image at a magnetic resonance imaging (MRI) system is provided. Accordingly, an analog signal based on a pulse sequence and a first gain is obtained. The analog signal is converted into a digitized signal. A potential quantization error is detected in the digitized signal based on a boundary. When the detection is affirmative, a replacement analog signal based on the pulse sequence is received. At least one portion of the replacement analog signal can be based on an adjusted gain. The adjusted gain is a factor of the first gain. The replacement analog signal is digitized into a replacement digitized signal. At least one portion of the replacement digitized signal corresponding to the at least one portion of the replacement analog signal is adjusted based on a reversal of the factor.

2 Claims, 11 Drawing Sheets

(51) Int. Cl.
   *H03M 1/18*     (2006.01)
   *G01R 33/36*    (2006.01)
   *A61B 5/055*    (2006.01)
   *G01R 33/54*    (2006.01)
   *G01R 33/565*   (2006.01)

(52) U.S. Cl.
   CPC ..... *G01R 33/4608* (2013.01); *G01R 33/4616* (2013.01); *G01R 33/54* (2013.01); *H03M 1/183* (2013.01); *G01R 33/565* (2013.01)

(58) Field of Classification Search
   USPC .................................................. 324/322, 318
   See application file for complete search history.

(56) References Cited

OTHER PUBLICATIONS

Extended European Search Report issued in relation to corresponding EP14901993.7 dated Jul. 27, 2018, 9 pgs.

* cited by examiner

SYSTEM AND METHOD FOR MAGNETIC RESONANCE IMAGE ACQUISITION

This application is a continuation of U.S. patent application Ser. No. 15/321,818 filed Sep. 15, 2014, the entire contents of which are hereby incorporated by reference.

FIELD OF THE INVENTION

The present invention relates generally to magnetic resonance imaging. More specifically, the present invention relates to a system and method for detecting errors in acquired signals.

BACKGROUND OF THE INVENTION

Magnetic resonance imaging (MRI) is a major imaging technique used in medicine. MRI is capable of generating detailed images of soft tissues such as the brain, muscles and kidneys. Specific properties of the various compounds found inside tissues, such as water and/or fat, are used to generate images. When subjected to a strong magnetic field, the vector sum of the nuclear magnetic moments of a large number of atoms possessing a nuclear spin angular momentum, such as Hydrogen, which is abundant in water and fat, will produce a net magnetic moment in alignment with the externally applied field. The resultant net magnetic moment will furthermore precess with a well-defined frequency that is proportional to the applied magnetic field. After excitation by radio frequency pulses, the net magnetization will generate a signal that can be detected.

Problems while detecting signals can cause an entire image to be corrupted. The corrupted images are typically not discovered until the scan is complete for the object, and images are presented for review to technicians and other qualified personnel. Given the scan times required for scanning an object, this can be quite costly. It would therefore be advantageous to be able to detect and potentially correct any anomalies prior to presenting the images of a completed scan for review.

SUMMARY OF THE INVENTION

It is an object to provide a novel system and method for an MRI scanning system and method that obviates and mitigates at least one of the above-identified disadvantages of the prior art.

According to an aspect, a method of acquiring an image at a magnetic resonance imaging (MRI) system is provided. The method can comprise receiving an analog signal based on a pulse sequence and a first gain. An analog to digital converter (ADC) can be used to digitize the analog signal into a digitized signal. A potential quantization error can be detected in the digitized signal based on a boundary. When the detecting is affirmative a replacement analog signal can be received based on the pulse sequence, at least one portion of the replacement analog signal being based on an adjusted gain, the adjusted gain being a factor of the first gain. The ADC can be used to digitize the replacement analog signal into a replacement digitized signal. At least one portion of the replacement digitized signal corresponding to the at least one portion of the replacement analog signal can be adjusted based on a reversal of the factor.

According to another aspect a second method of acquiring an image at a magnetic resonance imaging (MRI) system can be provided. The second method can comprise receiving raw data for the image. At least one indication of an event occurring at a time period can also be received. A portion of the raw data acquired can be determined to occur at a portion of the time period. When the determining is affirmative, a scan can be performed to obtain replacement data for the determined portion of the raw data.

These, together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION

Figure 1:
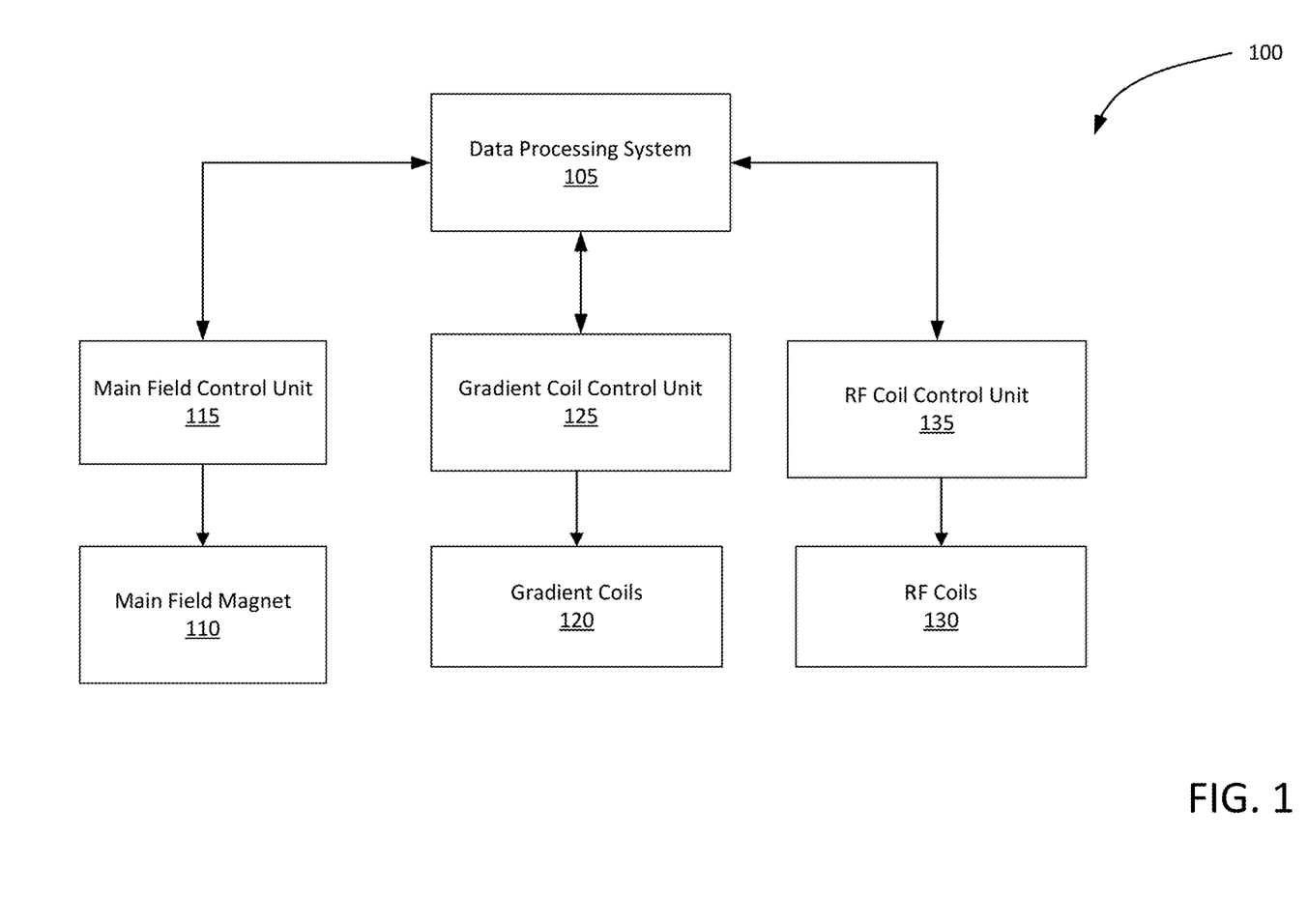
FIG. 1 shows a block diagram of functional subsystems of a magnetic resonance imaging system in accordance with an implementation.

Referring to FIG. 1, a block diagram of a magnetic resonance imaging (MRI) system, in accordance with an exemplary implementation, is shown at 100. The example implementation of the MRI system indicated at 100 is for illustrative purposes only, and variations including additional, fewer and/or varied components are possible. MRI is an imaging modality which is primarily used to construct pictures of nuclear magnetic resonance (NMR) signals from hydrogen atoms in an object. In medical MRI, typical signals of interest are NMR signals from water and fat, the major hydrogen containing components of tissues.

As shown in FIG. 1, the MRI system 100 comprises a data processing system 105. The data processing system 105 generally comprises one or more output devices such as a display, one or more input devices such as a keyboard and a mouse as well as one or more processors connected to a memory having volatile and persistent components. The data processing system 105 further comprises an interface adapted for communication and data exchange with the hardware components of the MRI system 100 used for performing a scan.

Continuing with FIG. 1, example the MRI system 100 also includes a main field magnet 110. The main field magnet 110 can be implemented as a permanent, superconducting or a resistive magnet, for example. Other magnet types, including hybrid magnets suitable for use in the MRI system 100 will now occur to a person of skill and are contemplated. The main field magnet 110 is operable to produce a substantially uniform magnetic field B0 having a direction along an axis. The magnetic field B0 is used to create an imaging volume within which desired atomic nuclei, such as the protons in Hydrogen within water and fat, of an object are magnetically aligned in preparation for a scan. In some implementations, as in this example implementation, a main field control unit 115 in communication with the data processing system 105 can be used for controlling the operation of the main field magnet 110.

The MRI system 100 further includes gradient coils 120 used for encoding spatial information in the main magnetic field B0 along, for example, three perpendicular axis. The size and configuration of the gradient coils 120 can be such that they produce a controlled and uniform linear gradient. For example, three paired orthogonal current-carrying gradient coils 120 located within the main field magnet 110 can be designed to produce desired linear gradient magnetic fields. The magnetic fields produced by the gradient coils 120, in combination and/or sequentially, can be superimposed on the main magnetic field B0 such that selective spatial excitation of objects within the imaging volume can occur. In addition to allowing spatial excitation, the gradient coils 120 can attach spatially specific frequency and phase information to the atomic nuclei, allowing the resultant MR signal to be reconstructed into a useful image. A gradient coil control unit 125 in communication with the data processing system 105 is used to control the operation of the gradient coils 120.

The MRI system 100 further comprises radio frequency (RF) coils 130. The RF coils 130 are used to establish a magnetic field B1 to excite the atomic nuclei or "spins". The RF coils 130 can also detect signals emitted from the "relaxing" spins within the object being imaged. Accordingly, the RF coils 130 can be in the form of separate transmit and receive coils or a combined transmit and receive coil with a switching mechanism for switching between transmit and receive modes.

The RF coils 130 can be implemented as surface coils, which are typically receive only coils and/or volume coils which can be receive and transmit coils. The RF coils 130 can be integrated in the main field magnet 110 bore. Alternatively, the RF coils 130 can be implemented in closer proximity to the object to be scanned, such as a head, and can take a shape that approximates the shape of the object, such as a close-fitting helmet. An RF coil control unit 135 in communication with the data processing system 150 is used to control the operation of the RF coils 130.

To create an image, the MRI system 100 detects the presence of atomic nuclei containing spin angular momentum in an object, such as those of hydrogen protons in water or fat found in tissues, by subjecting the object to a large magnetic field. In this example implementation the main magnetic field is denoted as B0 and the atomic nuclei containing spin angular momentum will be Hydrogen protons or simply protons. The Magnetic field B0 partially polarizes the Hydrogen protons in the object placed in the imaging volume of the main magnet 110. The protons are then excited with appropriately tuned RF radiation, in this example magnetic field B1. Finally, weak RF radiation signal from the excited protons is detected as they "relax" from the magnetic interaction. The frequency of the detected signal is proportional to the magnetic field to which they are subjected. Cross-section of the object from which to obtain signals can be selected by producing a magnetic field gradient across the object so that magnetic field values of B0 can be varied along various locations in the object. Given that the signal frequency is proportional to the varied magnetic field created, the variations allow assigning a particular signal frequency and phase to a location in the object. Accordingly, sufficient information can be found in the obtained signals to construct a map of the object in terms of proton presence, which is the basis of an MRI image. For example, since proton density varies with the type of tissue, tissue variations can be mapped as image contrast variations after the obtained signals are processed.

To obtain images from the MRI system 100 in the manner described above, one or more sets of RF pulses and gradient waveforms (collectively called "pulse sequences") are selected at the data processing system 105. The data processing system 105 passes the selected pulse sequence information to the RF control unit 135 and the gradient control unit 125, which collectively generate the associated waveforms and timings for providing a sequence of pulses to perform a scan.

Figure 2:
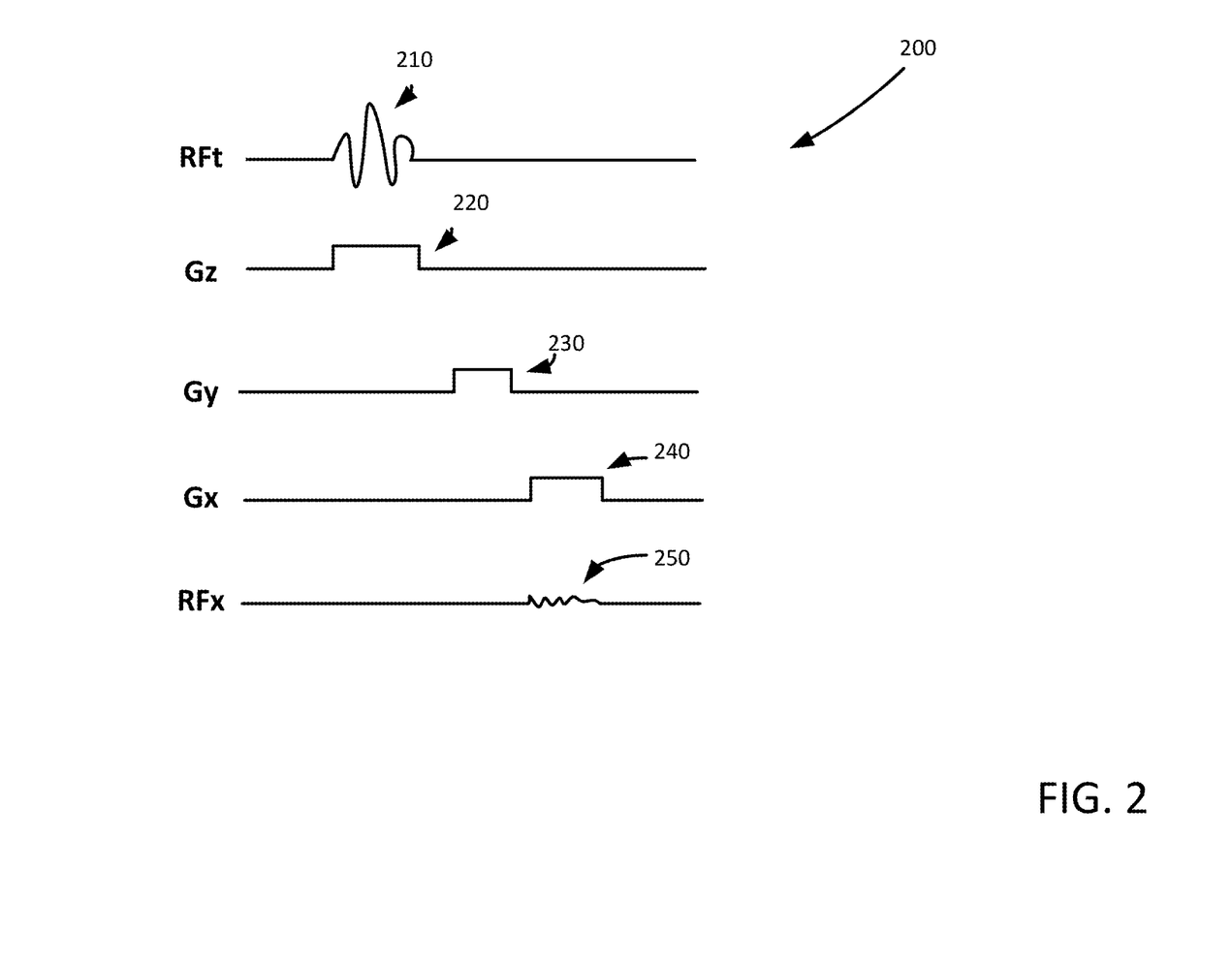
FIG. 2 shows an example pulse sequence in accordance with an implementation.

Referring now to FIG. 2, an illustrative pulse sequence 200 is shown that can be used to acquire images using the MRI system 100. Specifically, a timing diagram for the example pulse sequence is indicated. The timing diagram shows pulse or signal magnitudes, as a function of time, for transmitted RFt signal, magnetic field gradients $G_x$, $G_y$, and $G_z$, and received RFx signal. An idealized pulse sequence, simplified for illustrative purposes, contains a slice selection pulse 210 at RFt, a slice selection gradient pulse 220 at Gz, a phase encoding gradient pulse 230 at Gy, a frequency encoding gradient pulse 240 at Gx, as well as a detected signal 250 at RFx. The pulses for the three gradients Gx, Gy, and Gz represent the magnitude and duration of the magnetic field gradients generated by the gradient coils 120. The slice selection pulse 210 is generated by the transmit aspect of RF coils 130. Detected signal 250 is detected by the receive aspect of the RF coils 130. In this illustrative example it will be assumed that transmit aspect and receive aspect of RF coils 130 are formed by distinct coils.

The first event to occur in pulse sequence 200 is to turn on the slice selection gradient pulse 220. The slice selection pulse 210 is applied at the same time. In this illustrative example, the slice selection pulse 210 is a sin c function shaped burst of RF energy. In other implementations, other RF pulse shapes and durations can be used. Once the slice selection pulse 210 is turned off, the slice selection gradient pulse 220 is also turned off and a phase encoding gradient pulse 230 is turned on. Once the phase encoding gradient pulse 230 is turned off, a frequency encoding gradient pulse 240 is turned on and a detected signal 250 is recorded. It should be noted that the shapes, magnitudes and durations of the pulses and signals shown in FIG. 2 are chosen for illustrative purposes, and that in implementations, one or more of these factors and others may be varied to achieve the desired scan results.

The pulse sequence 200 is repeated a certain number of times, typically 256 times, to collect all the data needed to produce one image. The time between each repetition of the pulse sequence 200 is referred to as the repetition time (TR). Moreover, the duration between the center point of the slice selection pulse 210 and the peak of detected signal 250 is referred to as echo time (TE). Both TR and TE can be varied as appropriate for a desired scan. In some implementations, each time pulse sequence 200 is repeated, the magnitude of the phase encoding gradient pulse 230 is changed. For example, the magnitude can be changed in equal steps between a maximum amplitude and a minimum amplitude of the phase encoding gradient Gy. The variations in amplitude produce a variation in the phase of the precessing nuclei across the object being scanned, providing sufficient information for localization of detected signals 250 received for each repetition of pulse sequence 200. For example, pulse sequence 200 can be repeated 256 times with 256 equal magnitude steps of phase encoding gradient pulse 230 to obtain 256 distinct phase offsets containing spatial information in the direction of the phase encoding gradient field. If during the receive period of the pulse sequence, the detected signal 250 is sampled at 256 time points, an image containing 256×256 voxels within the selected slice can be produced after processing. The slice selection gradient pulse 220 can then be varied to acquire an image for a different slice. This process can continue until the desired number of slices are imaged.

Figure 3:
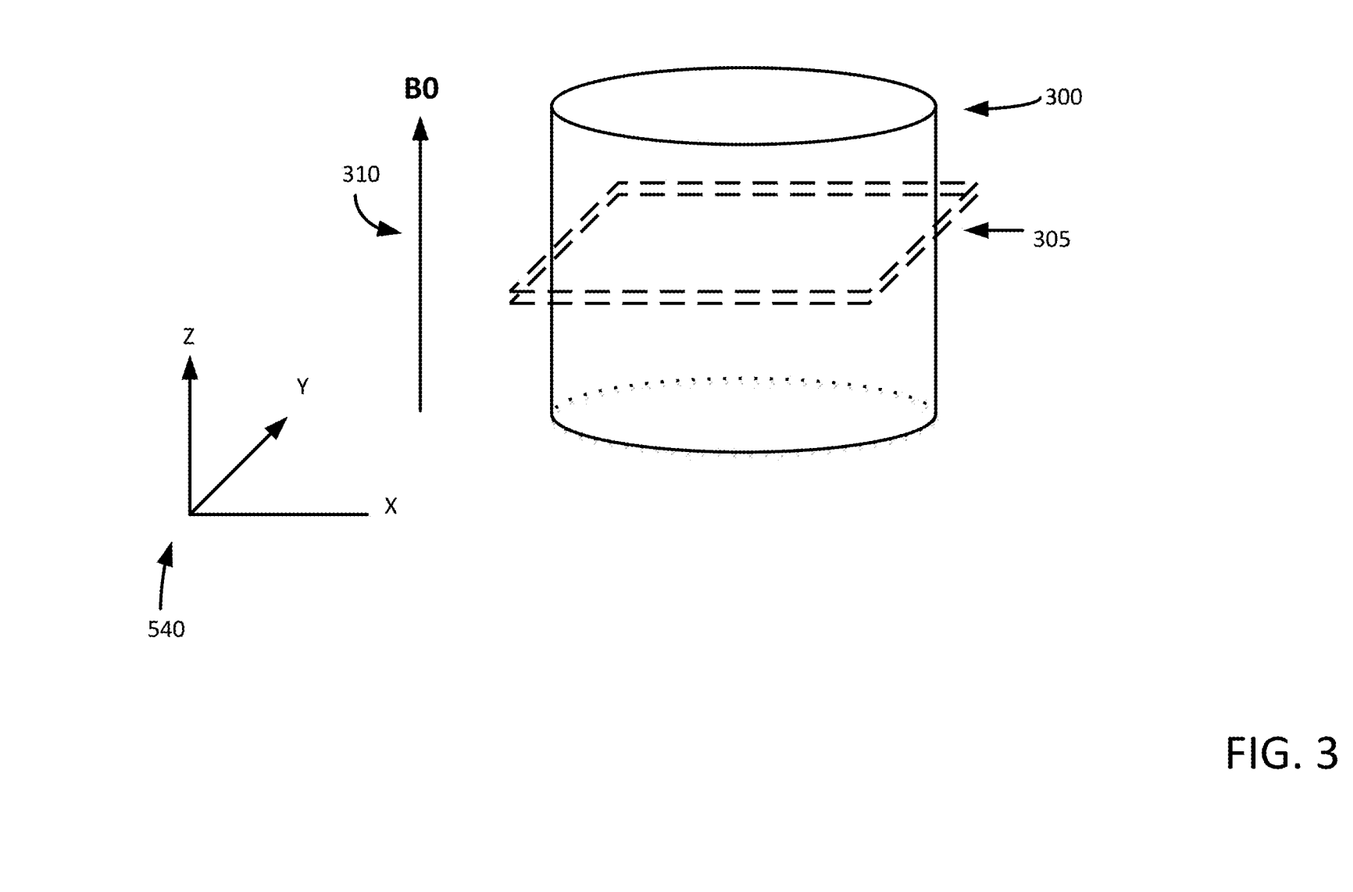
FIG. 3 shows an object and corresponding slice to be scanned by the magnetic resonance system of FIG. 1 in accordance with an implementation.

To further illustrate the signal acquisition process at the MRI system 100, it will be assumed that the object being imaged is a cylindrical object as indicated in FIG. 3 at 300. The object 300 has been placed within an external magnetic field B0 at 310, pointing along the Z-axis, and the object subsequently has a net magnetization vector. In this illustrative example, a slice in a plane along the X and Y axes as indicated at 305 is being imaged. It should be noted that in this example, the slice has a finite thickness along the Z-axis, creating a volumetric slice 305. To select a slice, the slice selection gradient pulse 220 is applied along the Z-axis, satisfying the resonance condition for the protons located in the slice 305. Indeed, the location of the slice along the Z-axis is determined based in part on the slice selective gradient pulse 220. Accordingly, the slice selection pulse 210, generated at the same time as the slice selection gradient pulse 220 excites protons that are located within the slice 305 in this example. Protons located above and below the slice 305 are not affected by the slice selection pulse 210.

Continuing with the illustrative example, in accordance with the pulse sequence 200, a phase encoding gradient pulse 230 is applied after the slice selection gradient pulse 220. Assuming this is applied along the Y-axis, the spins at different locations along the Y-axis begin to precess at different Larmor frequencies. When the phase encoding gradient pulse 220 is turned off, the net magnetization vectors at different locations precess at the same rate, but possess different phases. The phases are determined by the duration and magnitude of the phase encoding gradient pulse 230.

Once the phase encoding gradient pulse 230 is turned off, a frequency encoding gradient pulse 240 is turned on. In this example the frequency encoding gradient is in the X direction. The frequency encoding gradient causes protons in the selected slice to precess at rates dependent on their X location. Accordingly, different spatial locations within the slice are now characterized by unique phase angles and precessional frequencies. RF receive coils 130 are used to receive the detected signal 350 generated by the protons contained in the object being scanned while the frequency encoding gradient pulse 230 is turned on.

Figure 4:
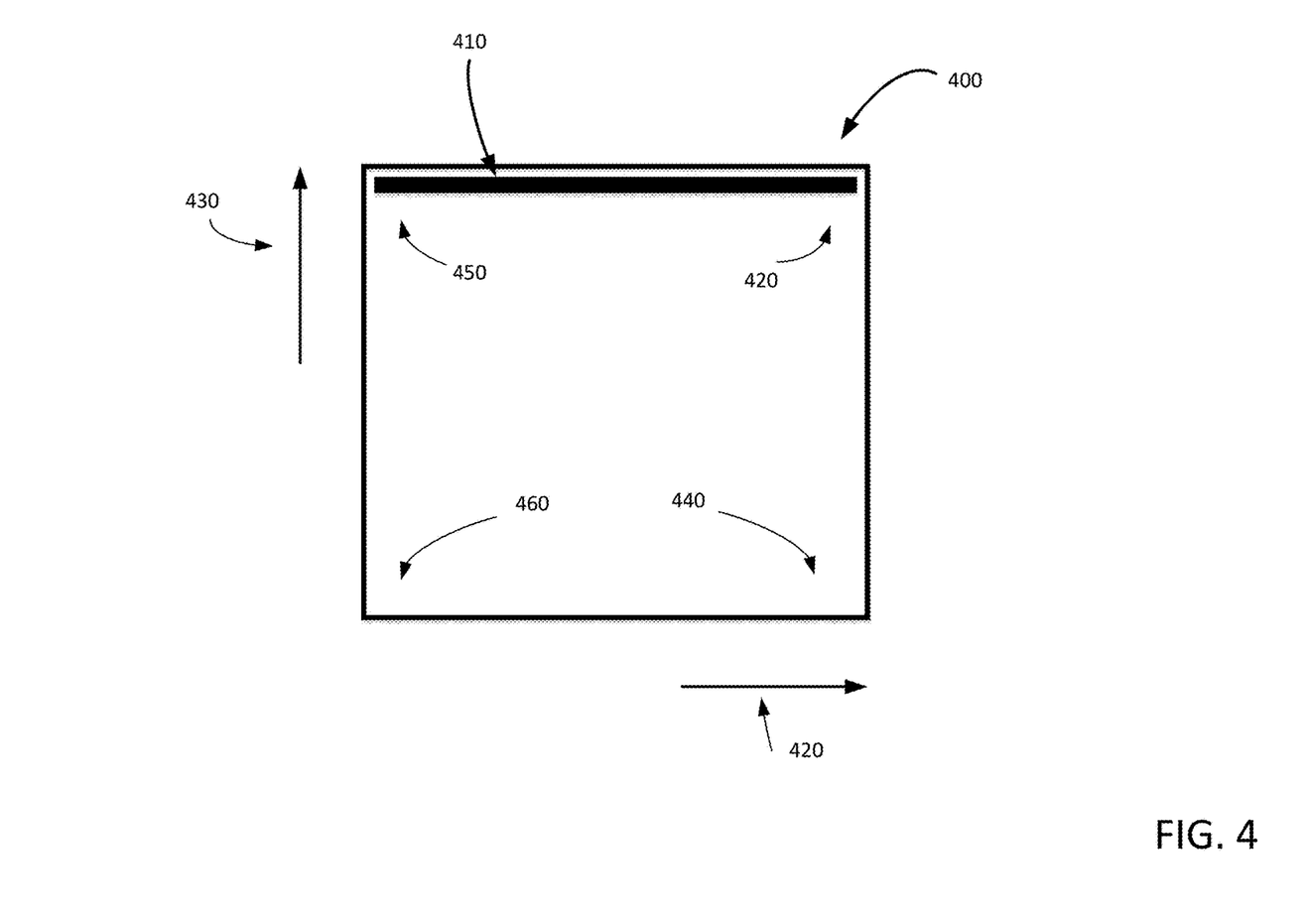
FIG. 4 shows a schematic representation of a k-space containing one received line in accordance with an implementation.

As the pulse sequence 200 is performed by MRI system 100, the acquired signals are stored in a temporary image space matrix referred to as k-space, as shown in FIG. 4 at 400. K-space is the collection of the detected signals measured for a scan and is in the spatial frequency domain. K-space is covered by frequency encoding data along the X-axis 420 (Kx) and phase encoding data along the Y-axis 430 (Ky). When all the lines for the k-space matrix for a slice are received (at the end of the scan of a single slice, for example) the data can be mathematically processed, for example through a two-dimensional Fourier-transform, to produce a final image. Thus, k-space holds raw data before reconstruction of the image into the spatial domain. Typically, k-space has the same number of rows and columns as the final image and is filled with raw data during the scan, usually one line per pulse sequence 200. For example, the first line of k-space 400, indicated at 410 is filled after the completion of the first pulse sequence generated for scanning a slice and contains the detected signal for that pulse sequence. It should be noted that other methods of filling k-space are possible, such as in a spiral manner, and are contemplated.

Figure 5:
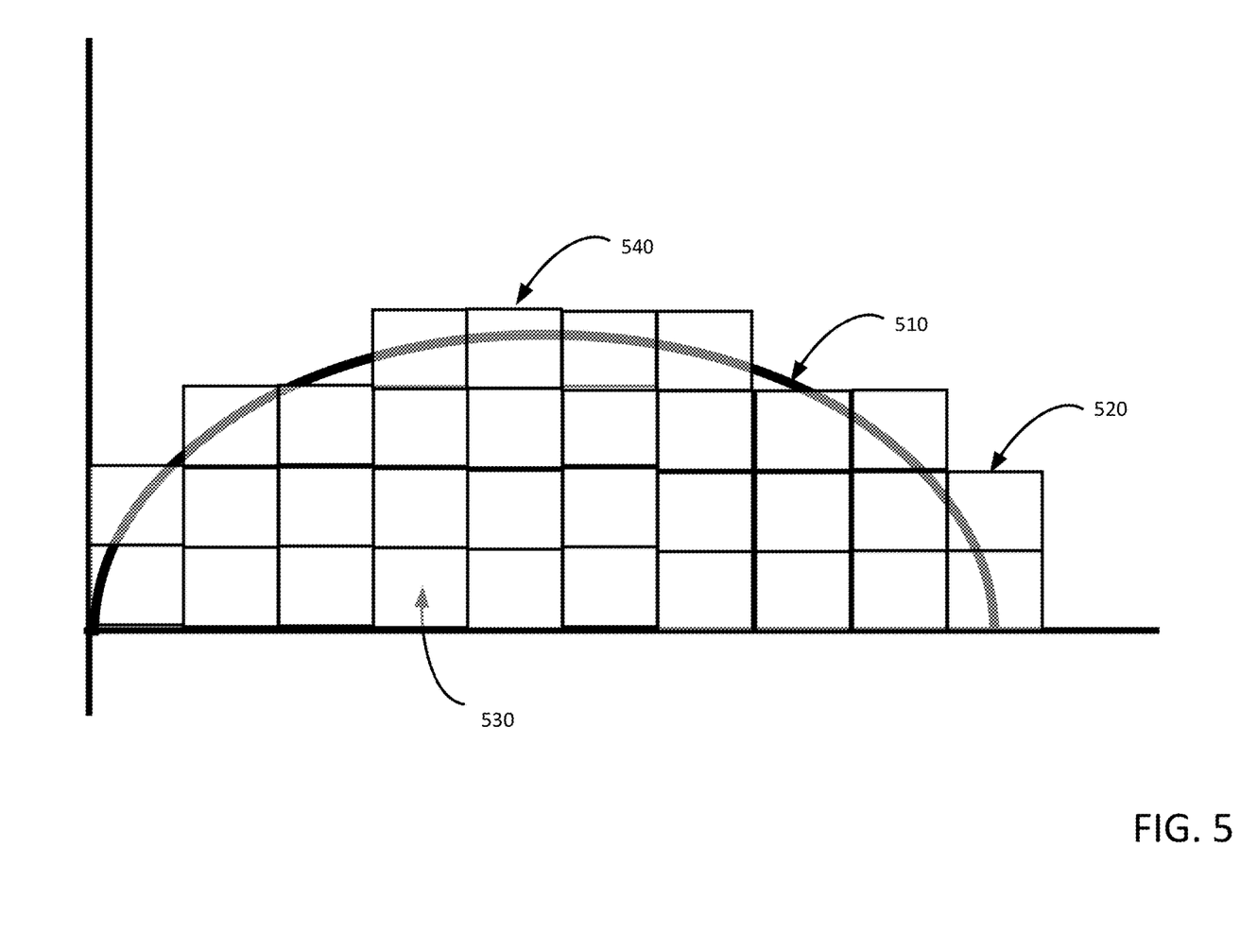
FIG. 5 shows a schematic representation of analog data and a corresponding digitized form in accordance with an implementation.

In some implementations, the MRI system 100 may be configured to dynamically respond to problems in the detected signals 250 in one or more pulse sequences and repeat the one or more pulse sequences as necessary. For example, a common problem in MRI systems is so-called "quantization noise". This noise typically arises from the rounding error between the analog input voltage to the analog to digital converter (ADC) and the output digitized value. For example, referring to FIG. 5, a line signal 510 corresponding to a portion of a detected signal 250 corresponding to one pulse sequence, for example, can be converted to a digital form 520 that can be used to populate one line of the k-space matrix, such as the line 410 of FIG. 4. It is to be understood that the signals and boundaries shown in this figure and the figures to follow are simplified for the purposes of illustration and are not meant to be limiting in scope. The horizontal center of each box 530 along the X-axis represents the time point at which the analog line signal 510 is sampled to obtain a digitized value. The height of each box 530 indicates the magnitude of quantization steps that are available to the ADC. For example, for an 8-bit ADC, a signal can be quantized into one of 256 different digitized values at a given time point. Accordingly, at time point 540, the line signal 510 has been discretized to have a value corresponding to four quantization steps.

Figure 6:
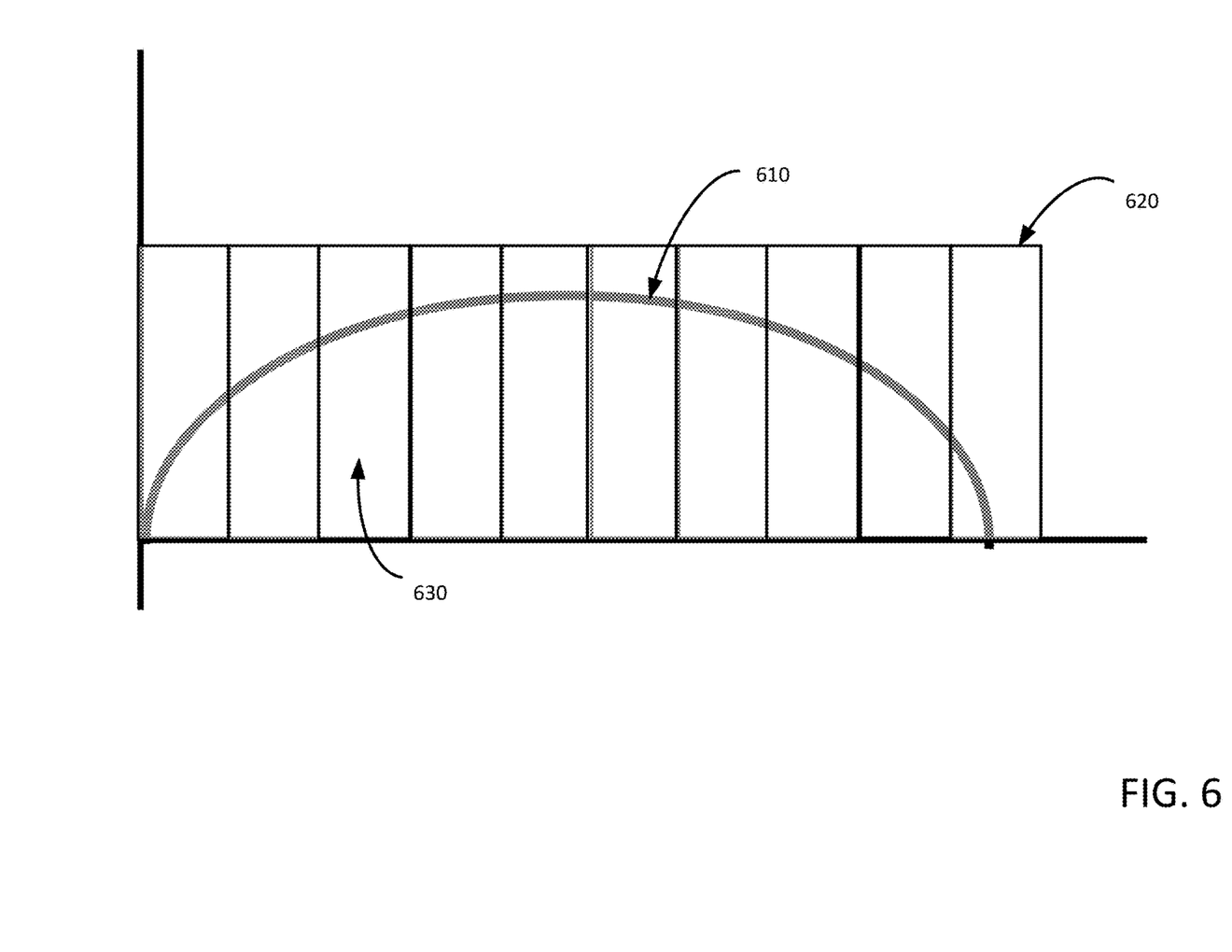
FIG. 6 shows a schematic representation of analog data and a corresponding digitized form in accordance with an implementation.

One problem with quantization is that when the amplitude range of a line signal is small in comparison to the magnitude of the quantization steps, signal shape information can be lost. For example, referring to FIG. 6, a line signal 610 is shown with respect to a digitized form 620, which was obtained using quantization steps corresponding to the height of each box 630. Since the amplitude of the line signal 620 is within the range of a single quantization step, all variations in the line signal 620 are lost in the digitized version 620.

Figure 7:
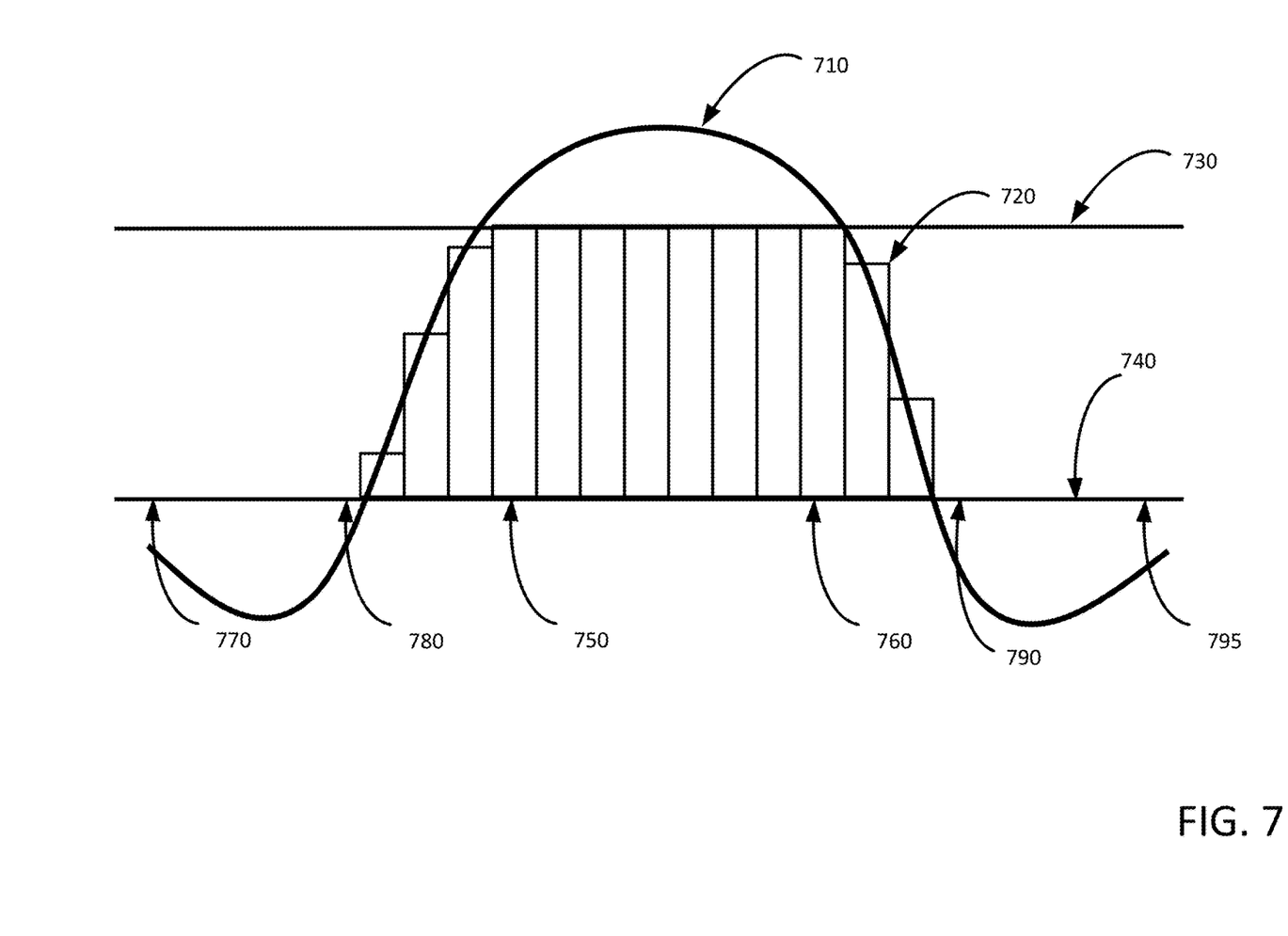
FIG. 7 shows a schematic representation of a line of raw data and a corresponding digitized form in accordance with an implementation.

In variations, where a signal range goes above or below the minimum or maximum amplitude an ADC can digitize, the digitized signal can be clipped at those points. For example, referring to FIG. 7, a line signal is shown at 710, with the corresponding digital signal shown at 720. Maximum and minimum amplitudes that can be digitized by the ADC are indicated at 730 and 740 respectively. As it can be seen, between the time points 750 and 760, the digital signal values are clipped at the maximum amplitude 730. On the other hand, the digital signal values are clipped at the minimum amplitude 740 between the time points 770 and 780 as well as 790 and 795.

Due to the methods used in reconstruction of a spatial image from the k-space matrix, such as Fourier Transforms, even a small anomaly such as quantization errors can corrupt an entire reconstructed image. As an example, the k-space for this illustrative example is taken to be a matrix with the dimensions of 256×256 cells corresponding to a final image resolution of 256×256 which is commonly used for MRI images. If a single cell of the k-space includes an erroneous value, that erroneous cell value can cause the entire resulting image for the slice to be corrupted. By constantly monitoring the detected signal 250, the MRI system 100 can detect potential quantization errors, and direct the system to correct the quantization error by, for example, repeating an appropriate section of the image scan. Given the times involved in acquiring image sets using an MRI system, having to repeat scans can be costly. The dynamic response to quantization errors can reduce the incidence of scans that need to be discarded due to artifacts To correct for quantization errors based on repeat partial scans, various methods can be used. Typically, prior to being digitized, a line signal is amplified through mechanisms which allow the gain of amplification to be varied, such a through the use of a variable gain amplifier. By changing the gain of the amplification, at least some of the problems associated with quantization errors can be alleviated. For example, the signal gain used for acquiring a line signal can be adjusted to compensate for at least portion of the problems. Accordingly, in one variation, for a line signal which has a low amplitude range in comparison with the operational amplitude range of the ADC, the gain can be increased to increase the amplitude range of the line signal to better correspond with that of the ADC. Alternatively, for a line signal which has a high amplitude range in comparison with the operational amplitude range of the ADC, the gain can be decreased to decrease the amplitude range of the line signal to better correspond with that of the ADC.

Figure 8:
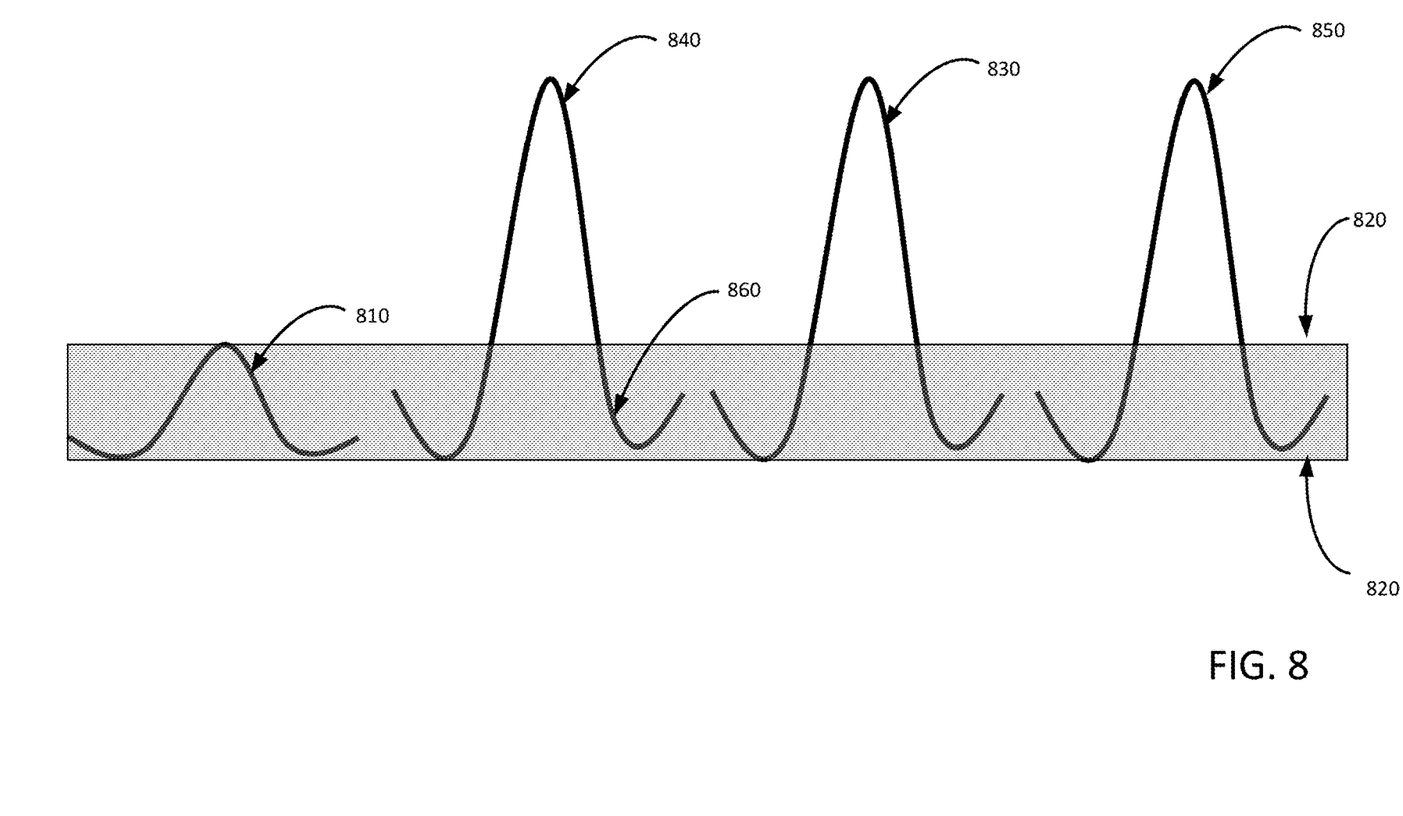
FIG. 8 shows a schematic representation of two lines of raw data and a corresponding adjusted forms in accordance with an implementation.

Referring to FIG. 8, an example is shown with respect to a line signal 810 which has a low amplitude range. The horizontal lines 820 indicate that the signal is within a single quantization step of the ADC. By increasing the gain when acquiring the line signal 810, the line signal 810 can be made to have an amplitude range that is significantly increased as indicated at 830. Indeed, the signal gain can be adjusted for each line signal separately such that each signal is altered by an amount that is appropriate for that line signal. For example, a second line signal 840 may not be adjusted at all, as indicated at 850.

One problem with applying a uniform signal gain adjustment for each line signal is that portions of the line signal may still be partially lost as indicated at 860. One method to address this issue can be to apply a signal gain that varies throughout portions of the line signal, as opposed to a uniform signal gain adjustment for the entire line signal. For example, referring back to FIG. 7, the gain can be increased for portions of the line signal 710 between the time points 770 and 780 as well as 790 and 795. On the other hand the gain may be decreased between the time points 750 and 760. The gain may be left the same for the remaining time points.

The MRI system 100 can be configured to detect, while signals are acquired, that one or more values in a line signal are potentially experiencing quantization errors. Accordingly, the MRI system 100 can dynamically evaluate the received information to detect potential quantization errors while the scan is progressing and the system can be configured to dynamically respond to detected potential errors, for example before the scan of an entire object is finished. For example, referring to FIG. 9, an analog line signal and its corresponding digitized form are shown at 910 and 920 respectively. A mask can be employed in the form of upper and lower boundaries, 930 and 940 respectively. The mask can be based on the amplitude range of ADC and the amplification gain mechanism employed by the MRI system 100. Accordingly, the mask may have an upper boundary of a certain percentage of the upper boundary of the ADC's operational amplitude range, for example 97% of the upper boundary of the ADC's operational amplitude range (the upper boundary of the ADC's operational amplitude range is not shown, but can be inferred by the clipped values for the digitized line signal 920 between the time points 960 and 970). Moreover, the mask may have a lower boundary based on the lower boundary of the ADC's operational amplitude range, as well as the operational gain range of the gain mechanism employed. For example, if the gain mechanism employed is operable to increase gain by up to %30, the lower boundary may be set to be 50% of the upper boundary of the ADC's operational amplitude range. The lower boundary of the ADC's operational range is indicated at the line 950.

Figure 9:
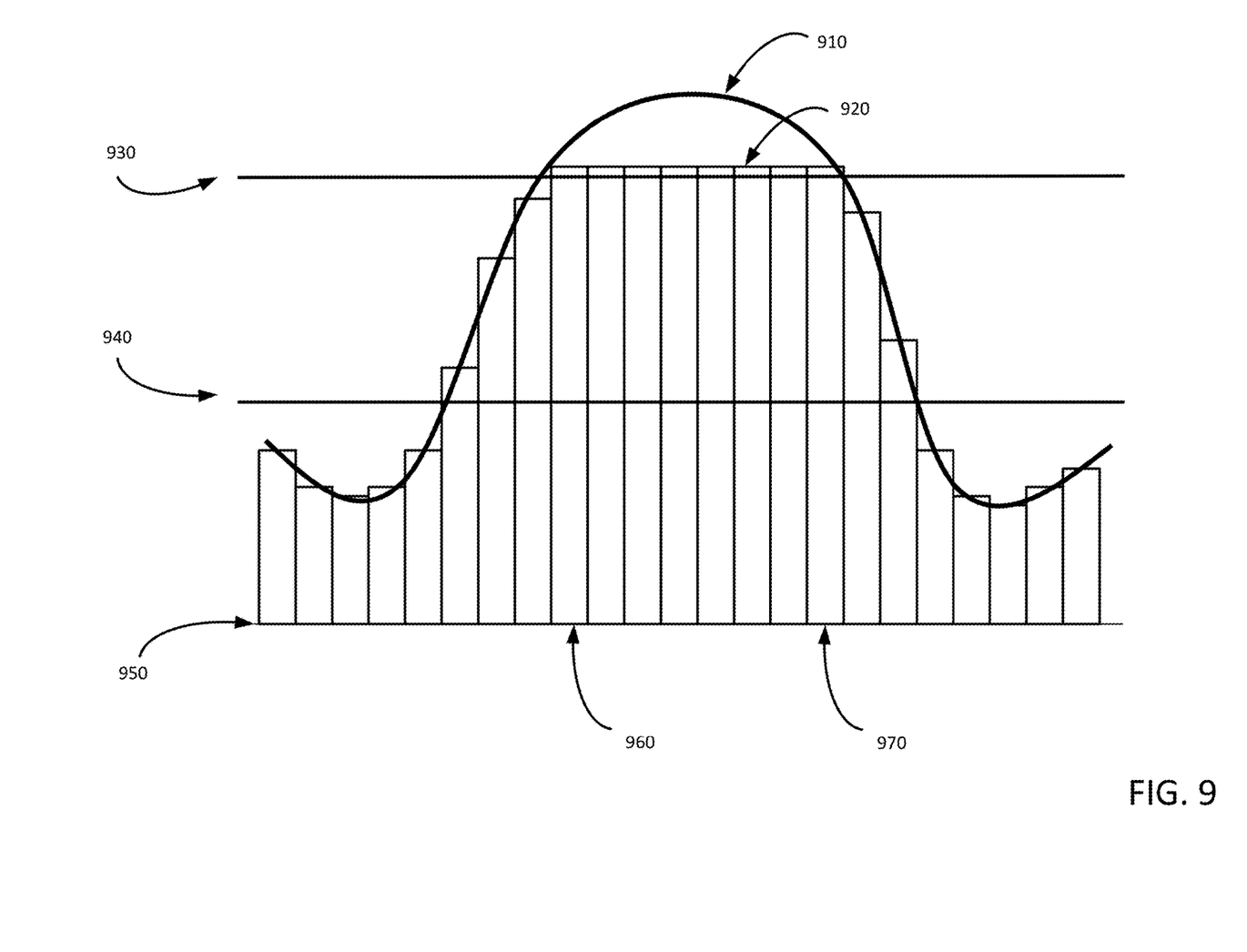
FIG. 9 shows a schematic representation of a line of raw data, its corresponding digitized form and boundaries in accordance with an implementation.

When the MRI system 100 detects digitized values of a digitized line signal at or above the upper mask boundary or at or below the lower mask boundary, the MRI system 100 can cause the line signal to be reacquired with the gains varied appropriately to correct for potential quantization errors, as described above.

Once the gain adjusted line signal is obtained and digitized, the gain adjustments can be corrected prior to using the digitized line signal as part of the k-space matrix. The correction can be a reversal of the gain adjustment. Accordingly, at any time point where an analog signal has been adjusted by increasing the gain by a certain factor, the value of the corresponding digitized signal at the same time point is decreased by a similar factor. Similarly, at any time point where an analog signal has been adjusted by decreasing the gain by a certain factor, the value of the corresponding digitized signal at the same time point is increased by a similar factor. For example, if a line signal is gain adjusted to alter the signal amplitude by a factor A, prior to digitizing, the digitized values for that line signal (or the values at relevant time points if not all of the line signal is gain adjusted) are divided by that factor A.

In some variations, the gain adjustments may cause phase changes in the signal when the signal is mapped to the k-space. Typically, the phase changes are based on an amount of gain adjustment. Accordingly, in these variations, the phase of the digitized signals (or signal portions) can be adjusted based on the amount of gain adjustment to correct for any phase errors introduced in this manner.

Figure 10:
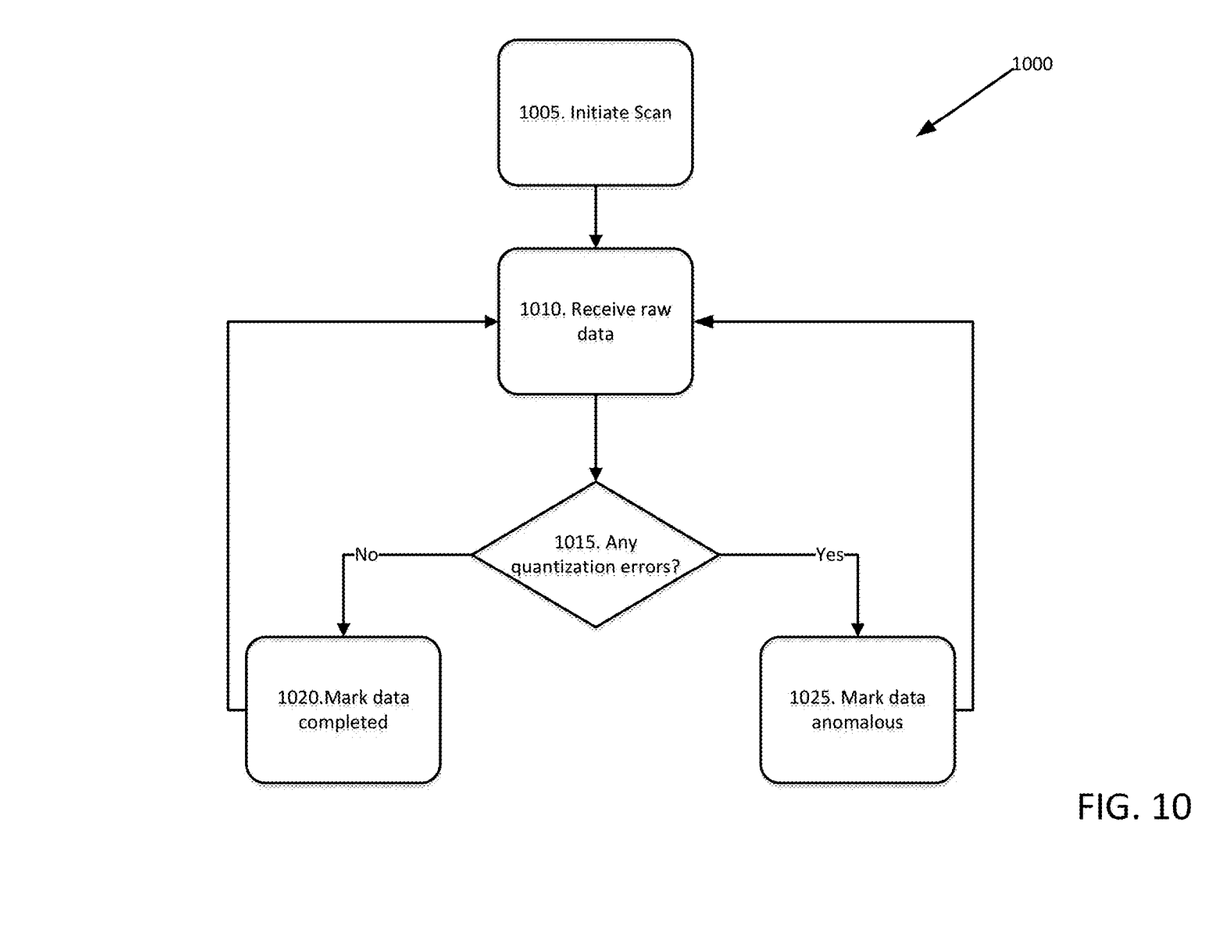
FIG. 10 shows a flow chart showing a method of detecting and correcting potential quantization errors in an MRI scan.

Referring now to FIG. 10, a method of detecting and correcting quantization errors is indicated generally at 1000. In order to assist in the explanation of the method, it'll be assumed that method 1000 is operated using the MRI system 100 as shown in FIG. 1. Additionally, the following discussion of method 1000 leads to further understanding of system 100. However, it is to be understood that system 100, and method 1000 can be varied, and need not work exactly as discussed herein in conjunction with each other, and that such variations are within scope.

Beginning first at 1005, a scan is initiated by performing a pulse sequence such as pulse sequence 200 as indicated in FIG. 2. At 1010, a portion of digitized raw data is received corresponding to the scan performed, as indicated at 1110 of FIG. 11. In this example, a line of the k-space matrix is received at the data processing system 105 as a result of performing the pulse sequence. The analog signal is indicated at 1110 and its corresponding digitized from at 1120. Line 1150 indicates the lowest boundary for the operational amplitude range of the ADC.

Figure 11:
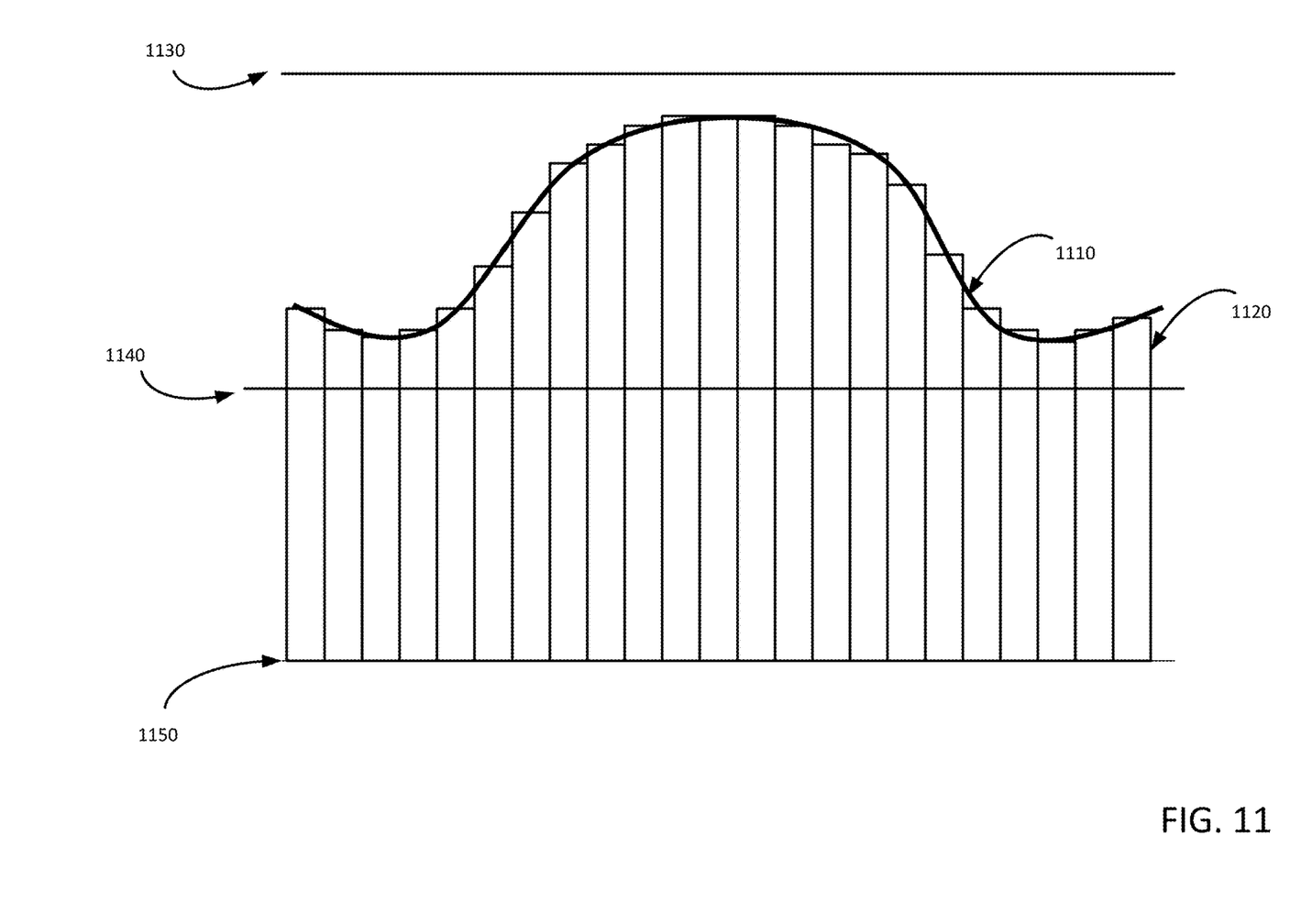
FIG. 11 shows a schematic representation of a line of raw data, its corresponding digitized form and boundaries in accordance with an implementation.

Referring back to FIG. 10, at 1015 a determination is made whether the received raw data contains any potential quantization errors. This determination can be made by the data processing system 105 on the basis of one or more methods used alone or in combination. For example, a predetermined mask or thresholds can be retrieved by the data processing system 105. Referring to FIG. 11, an example mask is indicated with upper and lower boundaries at lines 1130 and 1140 respectively. Once the mask is retrieved, the values of each of the cells of the signal 1120 is compared to the corresponding mask boundary values at that frequency to determine whether any of the scanned values are at the upper or lower boundaries of the mask values.

In this example implementation, all of the values of k-space signal are contained within the upper and lower mask boundaries, and thus the determination made is that minimal quantization errors exist in the digitized line signal 1120.

Continuing with the method 1000, once a determination is made that the line signal is within the upper and lower boundaries, at 1020 that line signal is marked as completed and scanning continues (if the specified scan is not completed for the entire object) with the next line.

Continuing at 1010, the next portion of raw data is received as a consequence of performing a scan using a second pulse sequence, different from the first pulse sequence. In this example, the result of the scan is the acquisition of a second line of k-space data at the data processing system 105, as shown in FIG. 9 at 910.

Referring back to FIG. 10, at 1015 a determination is made whether the digitized line signal, in this case line 920, contains any potential quantization errors. Example upper and lower boundary masks are indicated at lines 930 and 940 of FIG. 9, respectively. Line signal 910 indicates the analog signal from which digitized signal 920 is obtained. The values of each of the cells of the digitized line signal 920 is compared to the corresponding value of the mask boundary to determine whether any of the scanned values are above the upper boundary 930 or below the lower boundary 940 set by the mask boundary values. In this example implementation, numerous portions of the digitized line signal 920 is found to be above the upper boundary 930 or below the lower boundary 940 indicating that there is a potential quantization error in digitized line signal 920. Thus, a determination is made that quantization errors exist.

Continuing with method 1000, once a determination is made that quantization errors exist, at 1025 that digitized line signal is marked as anomalous and is caused to be rescanned using gain adjustments appropriate for correcting the potential quantization errors, as described above. The system can also log the occurrence of quantization errors so that a service team can be informed. The line that was detected as including an error can also be stored in memory for inspection by the service team.

In this illustrative example, digitized signal 920 is marked for rescanning and the method 1000 moves to 1010, repeating the scanning with the second pulse sequence, which is the same pulse sequence that was used to initially acquire raw data 910. Accordingly, replacement raw data for the digitized signal 920 is obtained at 1010. Once the replacement digitized line is obtained, the digitized values are corrected for gain adjustments and appropriate phase corrections. Method 1000 then continues until all k-space lines in all slices are acquired without any detected potential quantization errors. In some implementations, a maximum number of points that are allowed to be corrected, such as total number of quantization errors in a line, slice or number of slices, with this methodology can be specified. When the maximum number is reached, the data can be marked for performing a complete rescan or an error may be generated.

In a variation, the detection of quantization errors and/or replacement scans for detected quantization errors can be performed at the end of completing each k-space matrix for each slice, or even at the end of completing all k-space matrices for all desired slices. In these variations, the lines with detected anomalies can be rescanned by repeating the pulse sequences used for obtaining that line in the first place.

Although the illustrative example utilized line scans, other methods of gathering raw data, such as spiral acquisition of raw data can also be used. In these cases, the determination of quantization errors can be delayed until sufficient amount of data is obtained for performing line mask comparisons. Alternatively, differently shaped masks, developed to accommodate the particular scanning methodology can also be employed. These and other related variations that will now occur to a person of skill are contemplated.

In some variations, the method 1000 can be varied to account for events that are known to cause anomalies. Accordingly, at 1015, instead of checking for quantization errors, a check can be made to determine whether any events have occurred which are known to cause anomalies in a scan. For example, operational times of a robotic apparatus that may be used in the scanning room, may be detected. These times may be correlated with specific portions of the detected signal 250 which were known to have been acquired at corresponding time periods. Once such portions of the detected signal 250 are identified, the portions may be repeated to ensure that they are free of any anomalies. In variations, scanning operations may be halted while anomaly causing events are occurring.

Anomaly causing events may be detected based on various mechanisms and methods. For example, opening and closing of a door, which may introduce magnetic noise into the scanning room, may be detected through sensors placed on the door. Alternatively, a robot may provide indicators of its operation through various communication methods. Other variations will now occur to those of skill in the art.

Although the illustrative example utilized gradient-echo imaging, in other implementations method 1000 can be applied to other types of imaging methods such as multi-slice imaging, volume imaging or oblique imaging, spin-echo imaging, inversion recovery imaging and others that will now occur to a person of skill.

The above-described embodiments are intended to be examples and alterations and modifications may be effected thereto, by those of skill in the art, without departing from the scope which is defined solely by the claims appended hereto. For example, methods, systems and embodiments discussed can be varied and combined, in full or in part.

We claim:

1. A magnetic resonance imaging (MRI) system comprising a data processing system, an analog to digital converter (ADC), a main field magnet, gradient coils and radio frequency coils, the MRI system configured to perform a method comprising:
    receiving an analog signal based on a pulse sequence and a first gain;
    digitizing, by said ADC, the analog signal into a digitized signal;

detecting a potential quantization error in the digitized signal based on a boundary;

when the detecting is affirmative:

receiving a replacement analog signal based on the pulse sequence, at least one portion of the replacement analog signal being based on an adjusted variable gain, the adjusted gain being a factor of the first gain;

digitizing, by the ADC, the replacement analog signal into a replacement digitized signal; and adjusting at least one portion of the replacement digitized signal corresponding to the at least one portion of the replacement analog signal, based on a reversal of the factor.

2. A non-transient computer program product comprising computer executable instructions, the instructions, when executed by a computer, performing a method comprising:

receiving an analog signal based on a pulse sequence and a first gain;

digitizing, by a single analog to digital converter (ADC), the analog signal into a digitized signal;

detecting a potential quantization error in the digitized signal based on a boundary;

when the detecting is affirmative:

receiving a replacement analog signal based on the pulse sequence, at least one portion of the replacement analog signal being based on an adjusted variable gain, the adjusted gain being a factor of the first gain;

digitizing, by the ADC, the replacement analog signal into a replacement digitized signal; and adjusting at least one portion of the replacement digitized signal corresponding to the at least one portion of the replacement analog signal, based on a reversal of the factor.

* * * * *